(12) United States Patent
Jackson et al.

(10) Patent No.: US 10,235,754 B2
(45) Date of Patent: *Mar. 19, 2019

(54) SEMI-AUTOMATED HEART VALVE MORPHOMETRY AND COMPUTATIONAL STRESS ANALYSIS FROM 3D IMAGES

(71) Applicant: The Trustees of the University of Pennsylvania, Philadelphia, PA (US)

(72) Inventors: Benjamin M. Jackson, Wynnewood, PA (US); Robert C. Gorman, Lower Gwynedd, PA (US); Joseph H. Gorman, Lower Gwynedd, PA (US); Alison M. Pouch, Philadelphia, PA (US); Chandra M. Sehgal, Wayne, PA (US); Paul A. Yushkevich, Wynnewood, PA (US); Brian B. Avants, Philadelphia, PA (US); Hongzhi Wang, Boiling Springs, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/697,169

(22) Filed: Sep. 6, 2017

(65) Prior Publication Data

US 2017/0365057 A1 Dec. 21, 2017

Related U.S. Application Data

(63) Continuation of application No. 14/774,325, filed as application No. PCT/US2014/024082 on Mar. 12, 2014, now Pat. No. 9,779,496.

(Continued)

(51) Int. Cl.
*G06T 7/00* (2017.01)
*G06F 17/50* (2006.01)
(Continued)

(52) U.S. Cl.
CPC ............ *G06T 7/0012* (2013.01); *A61B 8/085* (2013.01); *A61B 8/0858* (2013.01);
(Continued)

(58) Field of Classification Search
CPC combination set(s) only.
See application file for complete search history.

(56) References Cited

U.S. PATENT DOCUMENTS 5,910,111 A * 6/1999 Hunziker ............... A61B 6/503
359/23
6,196,069 B1 * 3/2001 Wiedenmeier ........... G01N 3/20
73/81

(Continued)

OTHER PUBLICATIONS

Xu, et al., "A Novel Approach to in Vivo Mitral Valve Stress Analysis", Am. J. Physiol Heart Gire Physiol., 299(6), Oct. 2010, 1790-1794.

(Continued)

*Primary Examiner* — Tsung-Yin Tsai
(74) *Attorney, Agent, or Firm* — Baker & Hostetler LLP (57) ABSTRACT

A method is provided for measuring or estimating stress distributions on heart valve leaflets by obtaining three-dimensional images of the heart valve leaflets, segmenting the heart valve leaflets in the three-dimensional images by capturing locally varying thicknesses of the heart valve leaflets in three-dimensional image data to generate an image-derived patient-specific model of the heart valve leaflets, and applying the image-derived patient-specific model of the heart valve leaflets to a finite element analysis (FEA) algorithm to estimate stresses on the heart valve leaflets. The images of the heart valve leaflets may be obtained using real-time 3D transesophageal echocardiography (rt-3DTEE). Volumetric images of the mitral valve at mid-systole may be analyzed by user-initialized segmentation and 3D deformable modeling with continuous medial (Continued)

representation to obtain, a compact representation of shape. The regional leaflet stress distributions may be predicted in normal and diseased (regurgitant) mitral valves using the techniques of the invention.

18 Claims, 3 Drawing Sheets

Related U.S. Application Data (60) Provisional application No. 61/788,691, filed on Mar. 15, 2013.

(51) Int. Cl.
*A61B 8/08* (2006.01)
*A61B 8/12* (2006.01)
*G06K 9/46* (2006.01)
*G06K 9/52* (2006.01)
*G06K 9/62* (2006.01)
*G06T 3/40* (2006.01)
*G06T 7/60* (2017.01)
*G06T 7/13* (2017.01)

(52) U.S. Cl.
CPC .............. *A61B 8/0883* (2013.01); *A61B 8/12* (2013.01); *A61B 8/483* (2013.01); *G06F 17/5018* (2013.01); *G06K 9/4604* (2013.01); *G06K 9/52* (2013.01); *G06K 9/6215* (2013.01); *G06T 3/40* (2013.01); *G06T 7/13* (2017.01); *G06T 7/60* (2013.01); *A61B 8/485* (2013.01); *G06K 2009/4666* (2013.01); *G06T 2200/04* (2013.01); *G06T 2207/10136* (2013.01); *G06T 2207/20112* (2013.01); *G06T 2207/30048* (2013.01)

(56) References Cited

U.S. PATENT DOCUMENTS

| | | | |
|---|---|---|---|
| 7,693,563 B2 | 4/2010 | Suresh et al. | |
| 7,828,735 B2* | 11/2010 | Holmes | A61B 5/055 600/450 |
| 8,920,322 B2* | 12/2014 | Mansi | A61B 8/0883 600/437 |
| 2004/0153128 A1* | 8/2004 | Suresh | G06F 19/3481 607/14 |
| 2005/0187461 A1* | 8/2005 | Murphy | G09B 23/28 600/416 |
| 2006/0149522 A1* | 7/2006 | Tang | G06F 19/321 703/11 |
| 2007/0014452 A1* | 1/2007 | Suresh | G06F 19/3481 382/128 |
| 2007/0208550 A1* | 9/2007 | Cao | A61F 2/2412 703/11 |
| 2008/0319308 A1* | 12/2008 | Tang | A61B 5/055 600/416 |
| 2010/0016711 A1* | 1/2010 | Kheradvar | A61B 5/05 600/425 |
| 2011/0142316 A1* | 6/2011 | Wang | G06T 11/006 382/131 |
| 2012/0232853 A1* | 9/2012 | Voigt | G06F 19/321 703/1 |
| 2013/0052155 A1* | 2/2013 | Marcolongo | C08B 37/003 424/78.27 |
| 2013/0195335 A1* | 8/2013 | Gorman | G06T 7/0012 382/131 |
| 2014/0071125 A1* | 3/2014 | Burlina | G06T 17/00 345/420 |
| 2014/0357938 A1* | 12/2014 | Pilla | A61M 1/122 600/17 |
| 2015/0178938 A1* | 6/2015 | Gorman, III | G06T 7/174 382/131 |
| 2015/0305706 A1* | 10/2015 | Kanik | A61B 8/0883 600/438 |

OTHER PUBLICATIONS

Votta, et al., "Mitral Valve Finite-Element Modeling from Utrasound Data: A Pilot Study for a New Approach to Understand Mitral Function and Clinical Scenarios", Philosophical Transactions Series A, Mathematical, Physical, and Engineering Sciences, 366,Jul. 2008, 3411-3434.

Rausch, et al., "Mechanics of the Mitral Valve", Biomech Model Mechanobiol., Dec. 2012, vol. 12, 1053-1071.

Prot, et al., "Finite Element Analysis of the Mitral Apparatus: Annulus Shape Effect and Chordal Force Distribution", Biomechanics and Modeling in Mechanobiology, Jan. 2008, vol. 8, 43-55.

Pouch AM et al. Journal of Biomechanics. "Semi-automated mitral valve morphometry and computational stress analysis using 3D ultrasound". Mar. 15, 2012 vol. 45(5): pp. 903-907. Epub Jan. 26, 2012; abstract.

* cited by examiner

SEMI-AUTOMATED HEART VALVE MORPHOMETRY AND COMPUTATIONAL STRESS ANALYSIS FROM 3D IMAGES

CROSS-REFERENCE TO RELATED APPLICATIONS

This application is a continuation of U.S. Ser. No. 14/774,325, filed Sep. 10, 2015, which is the U.S. National Stage of International Application No. PCT/US2014/024082, filed Mar. 12, 2014, which claims the benefit of U.S. Provisional Application No. 61/788,691 filed Mar. 15, 2013, the entire disclosures of each of which are incorporated herein by reference for any and all purposes.

TECHNICAL FIELD

The invention relates to methods of analyzing heart valves using 3D images of the heart valves and, more particularly, to techniques for semi-automating the process of providing heart valve morphometry for computational stress analysis using 3D ultrasound.

BACKGROUND

Mitral valve (MV) disease is common in humans and not infrequently fatal. Mitral regurgitation, in particular, demonstrates a strongly-graded relationship between severity and reduced survival. MV surgery, both repair and replacement, are commonly exercised treatment options for mitral regurgitation. Imaging and assessment of the mitral valve has traditionally been achieved by qualitative 2D ultrasound image analysis. Recently, real-time three-dimensional transesophageal echocardiography (rt-3DTEE) has become widely available and implemented. 3D image-based modeling of the mitral valve is increasingly useful, and finite element analysis (FEA) has been applied to the MV frequently over the last 20 years.

To date, the majority of valve morphometry studies have employed manual tracing to reconstruct valve geometry from 3D echocardiographic image data. Therefore, the first objective herein is to introduce an alternative semi-automated approach to valve morphometry based on a simple and rapid approach to user-initialized image segmentation that exploits the contrast between the mitral valve tissue and surrounding blood pool in rt-3DTEE images. The valve is subsequently modeled using 3D continuous medial representation to obtain localized thickness maps of the mitral leaflets.

The inventors recently provided a framework for the application of in vivo MV geometry and FEA to human MV physiology, pathophysiology, and repair. (see, Xu C, Brinster C J, Jassar A S, et al. A novel approach to in vivo mitral valve stress analysis. Am J Physiol Heart Circ Physiol. 299(6):1790-1794, 2010). Therefore, a second objective herein is to demonstrate that the semi-automated 3D MV model can be loaded with physiologic pressures using FEA, yielding reasonable and meaningful stress and strain magnitudes and distributions. Furthermore, the inventors endeavor to demonstrate this capability in both healthy and diseased human mitral valves. The methods of the invention address these and other objectives.

SUMMARY

Particular embodiments of the methods of the invention use high-resolution image-derived geometric models of the mitral valve as anatomically accurate input to finite element analysis (FEA) in order to estimate localized stress distributions on the mitral leaflets. A key property of the models is that they volumetrically represent the leaflets (as structures with locally varying finite thickness). All previous studies have made very generic assumptions of leaflet thickness in their FEA studies. For example, leaflet thickness was assumed to be uniform or have a generic, uniformly distributed thickness pattern. These assumptions have been based primarily on ex vivo analysis of porcine valve tissue, rather than in vivo human valve tissue. A recent review by Rausch et al. ("Mechanics of the Mitral Valve", Biomech Model Mechanobiol. 2012) indicates that leaflet thickness is one of the most influential parameters in biomechanical simulations of the mitral valve, which supports the relevance and significance of the volumetric models as described herein. The methods of the invention thus assess valve morphology and thickness in vivo in order to measure or estimate the stresses on mitral valve leaflets to improve mitral valve repair durability. As will be apparent to those skilled in the art from the following description, the techniques described herein need not be limited to mitral valve leaflets but may also be applied to other heart valve leaflets.

Exemplary embodiments of the method of the invention relate to measuring or estimating stress distributions on heart valve (e.g., mitral valve) leaflets to, for example, improve heart valve repair durability by obtaining three-dimensional images of the heart valve leaflets, segmenting the heart valve leaflets in the three-dimensional images by capturing and/or quantifying locally varying thicknesses of the heart valve leaflets in three-dimensional image data to generate an image-derived patient-specific model of the heart valve leaflets, and applying the image-derived patient-specific model of the heart valve leaflets to a finite element analysis (FEA) algorithm to estimate stresses on the heart valve leaflets. The patient-specific model of the heart valve leaflets may be applied to the FEA algorithm using image-derived thickness measurements of the heart valve leaflets as input material parameters. The images may be obtained by a number of techniques including three-dimensional echocardiography.

Segmenting the heart valve leaflets may be performed manually, with active contour evolution, with multi-atlas segmentation, or with a deformable modeling method. For example, user-initialized three-dimensional active contour evolution based on region competition may be used to segment the heart valve leaflets in the three-dimensional image data. User-initialized regional of interest (ROI) extraction may include construction of a two-dimensional maximum intensity projection image along an axial dimension of the image volume of the heart valve leaflet images and application of adaptive histogram equalization to the projection image to enhance an annular rim and leaflet coaptation zone of the heart valve. The user may outline the heart valve and mark a leaflet coaptation curve in the enhanced projection image, select a threshold for region competition, and use the resulting information to initialize three-dimensional active contour segmentation. The level set method may be used to solve for the final three-dimensional segmentation.

The user-initialized segmentation method may be used to obtain three-dimensional binary images of the anterior and posterior leaflets of the mitral valve, from which localized measurements of leaflet thickness can be computed. To obtain localized leaflet thickness measurements, the shape of each heart valve leaflet may be modeled with three-dimensional continuous medial representation (cm-rep). A patient-specific cm-rep of the heart valve leaflets may be obtained by fitting a deformable medial model (a cm-rep template of the heart valve leaflets) to binary segmentations of the heart valve leaflets by Bayesian optimization. Each heart valve leaflet may be treated as a separate shape, whose morphological skeleton comprises a single medial manifold. The medial manifold and surface boundaries of the cm-rep of each heart valve leaflet may be discretely represented by a triangulated mesh. Each node of the medial mesh may quantify a localized leaflet thickness measurement, defined as the chord length or distance between two boundary points associated with that node on medial mesh. During Bayesian optimization, the mesh of each heart valve leaflet may be deformed such that the similarity between the leaflet mesh and its corresponding segmentation is maximized. For increased efficiency during model fitting, a Laplace eigenfunction basis may be defined on the medial mesh such that the medial mesh is deformed smoothly by modifying coefficients of a small number of basis functions rather than all vertices of the mesh. Model fitting may be performed in stages with increasing resolution to enhance model fitting accuracy and speed. In an exemplary embodiment, an atrial surface of the fitted cm-rep of each mitral valve leaflet is applied to the FEA algorithm for finite element analysis, using locally defined leaflet thickness at each point on the atrial surface as input information.

BRIEF DESCRIPTION OF THE DRAWINGS

The various novel aspects of the invention will be apparent from the following detailed description of the invention taken in conjunction with the accompanying drawings, of which.

DETAILED DESCRIPTION OF ILLUSTRATIVE EMBODIMENTS

The invention will be described in detail below with reference to FIGS. 1-5. Those skilled in the art will appreciate that the description given herein with respect to those figures is for exemplary purposes only and is not intended in any way to limit the scope of the invention. All questions regarding the scope of the invention may be resolved by referring to the appended claims. For example, though mitral valves are discussed exclusively in the exemplary embodiment, it will be appreciated that the techniques described herein may be applied to other heart valves as well.

Methods

Image Acquisition

Intra-operative rt-3DTEE data sets were obtained from two patients, one with severe ischemic mitral regurgitation (IMR) and one without mitral valve disease. The electrocardiographically gated images were acquired with an iE33 scanner (Philips Medical Systems, Andover, Mass.) using a 2 to 7 MHz transesophageal matrix-array transducer over four consecutive cardiac cycles. The frame rate was 17 to 30 Hz with an imaging depth of 14 to 17 cm. The image volumes were exported in Cartesian format (224×208×208 voxels), with an approximate isotropic resolution of 0.7 mm. From each rt-3DTEE data series, an image volume delineating the mitral valve at mid-systole (a single time point in the cardiac cycle) was selected for analysis.

Semi-Automated Image Analysis

User-Initialized Segmentation

Segmentation of the mitral leaflets in accordance with the inventive technique has two steps: user-initialized region of interest (ROI) extraction, and 3D active contour segmentation based on region competition. User-initialized ROI extraction begins with construction of a 2D maximum intensity projection image along the axial dimension of the image volume. Adaptive histogram equalization is applied to the projection image to enhance the annular rim and leaflet coaptation zone of the mitral valve. In this enhanced projection image, a user outlines the valve and marks the leaflet coaptation curve in 2D. This information is then used to initialize 3D segmentation. The user selects a soft threshold for region competition, and a level set method is used to perform the final segmentation. The segmentation process is illustrated in FIG. 1, and the anterior and posterior leaflet segmentations of the normal and diseased subjects are illustrated in FIG. 2(a).

Figure 1:
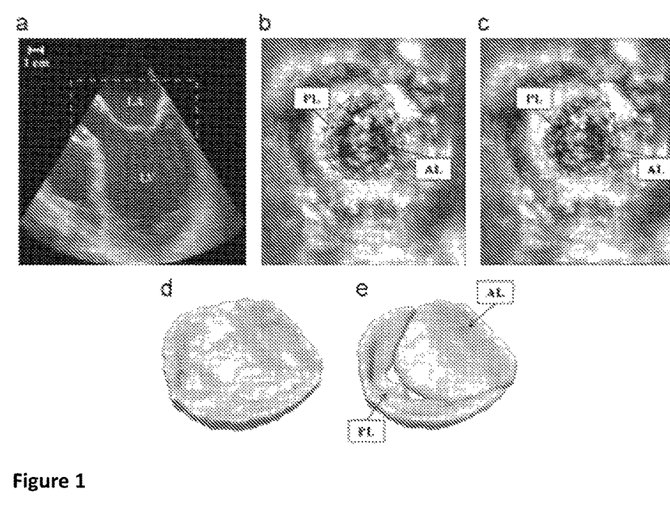
FIG. 1 illustrates application of a semi-automated segmentation algorithm in an exemplary embodiment.

FIG. 1 illustrates application of a semi-automated segmentation algorithm in an exemplary embodiment. In FIG. 1(a), the user initializes an ROI in a long-axis cross-section of the 3DE image volume, identifying the valve along the axial dimension. In FIG. 1(b), the user initializes annular points in a projection image depicting the valve from an atrial perspective. In FIG. 1(c), the user shifts posterior annular points into the coaptation zone, forming an outline of the anterior leaflet. In FIG. 1(d), the user initialization is used to automatically generate a 3D ROI containing the valve in the image volume. Finally, in FIG. 1(e), a final segmentation of the valve is obtained by thresholding and 3D active contour evolution. (LA=left atrium, LV=left ventricle, AL=anterior leaflet, PL=posterior leaflet).

Figure 2:
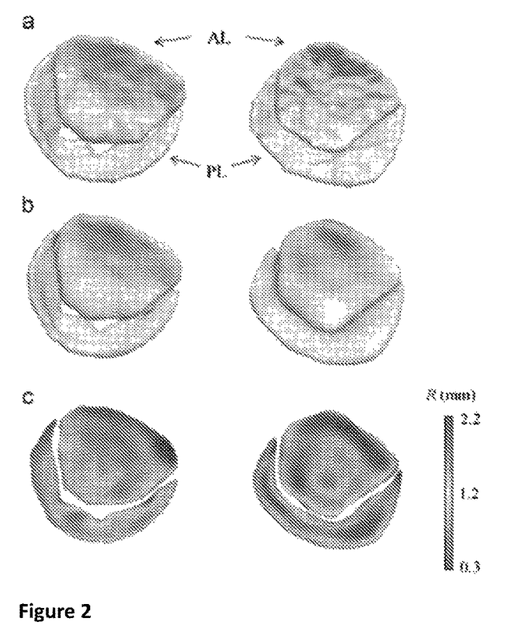
FIG. 2 illustrates reconstructions of mid-systolic diseased (left) and normal (right) mitral valves from 3DE image data, including (a) the results of image segmentation, (b) the fitted medial models, and (c) the radial thickness field R mapped to the medial manifold of each leaflet.

FIG. 2 illustrates reconstructions of mid-systolic diseased (left) and normal (right) mitral valves from 3DE image data, including (a) the results of image segmentation, (b) the fitted medial models, and (c) the radial thickness field R mapped to the medial manifold of each leaflet. Note that, by definition, the medial manifold does not extend to the leaflet boundary, as there is a distance R between the manifold and leaflet surface. (AL=anterior leaflet, PL=posterior leaflet).

Mitral Valve Geometric Modeling

Once 3D binary images of the anterior and posterior leaflets are obtained, the method of the invention is used to model the shape of each mitral leaflet using 3D continuous medial representation (cm-rep). Those skilled in the art will appreciate that the images may be obtained using other imaging methods besides echocardiography and that other segmentation methods, such as multi-atlas segmentation, may also be applied before the cm-rep model fitting step. Unlike a surface representation that describes an object's boundary geometry, medial representation is a compact representation of shape. First introduced by Blum, a shape's medial axis is defined as the locus of centers of maximal inscribed balls (MIBs), where each ball is tangent to the object's boundary at a minimum of two points. In three dimensions, a medial representation is a locus of tuples $(m,R) \varepsilon \mathbb{R}^8 \times \mathbb{R}^8$, where m is the medial manifold formed by the centers of the MIBs and R refers to the radii of the MIBs centered at those points or, equivalently, to the distance between the medial axis and object surface. For reference, a 2D diagram of medial representation is presented in FIG. 3. Medial representation is exploited herein for its ability to assess local variations in leaflet thickness, derived from the radial thickness field R.

Figure 3:
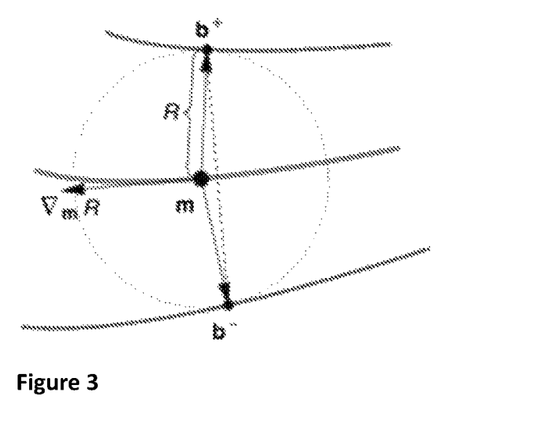
FIG. 3 illustrates a two-dimensional diagram of medial geometry.

FIG. 3 illustrates a two-dimensional diagram of medial geometry. The curve through m represents the medial surface (skeleton) m. The maximally inscribed circle centered at the dot on m has radius R, with two spokes (arrows) pointing to two points, $b^+$ and $b^-$, on the object boundaries (curves through $b^+$ and $b^-$). The vector $\nabla_m R$ lies in the tangent plane of m and points in the direction of greatest change in R. Thickness is measured herein as chord length, illustrated by the dotted line spanning the distance between $b^+$ and $b^-$.

In the cm-rep framework, geometric representations of the mitral leaflets are obtained by fitting a deformable medial model, also referred to as a template, to its binary segmentation by Bayesian optimization. Each leaflet is treated as a separate shape, so the valve is modeled as two separate cm-reps, where each leaflet is a simple object whose skeleton consists of a single medial manifold. The medial manifold of each leaflet is represented by a mesh with 500 to 600 nodes and 900 to 1000 triangulated elements and is associated with a triangulated boundary mesh that represents the surface of the leaflet. Template fitting, or mesh deformation, consists of three stages: one alignment stage, one multi-resolution fitting stage, and a final deformation stage where both leaflets are simultaneously fitted to the leaflet segmentations. (1) During the first stage, Jenkinson's FLIRT affine registration tool is used to obtain a similarity transform that aligns the leaflet templates with their corresponding segmentations. (2) The leaflet medial models are then independently deformed to fit the binary leaflet segmentations at three different resolutions. The objective function minimized during deformation incorporates the volumetric overlap error between the medial model and binary segmentation, as well as regularization terms and inequality constraints required by inverse skeletonization. (3) Finally, to correct for any intersection of the leaflet models, the medial models of the two leaflets are combined into a single model during the third stage of fitting. During the simultaneous fitting of both leaflets, a leaflet intersection penalty term is used to correct and prevent intersection of the leaflets' medial models. For increased efficiency during the last two steps of template fitting, the Laplace eigenfunction basis is defined on the medial template such that it can be deformed smoothly by modifying the coefficients of a small number of basis functions rather than all vertices of the template mesh. The results of model fitting are shown in FIG. 2(b), and the radial thickness field R mapped to the medial manifold of each leaflet is shown in FIG. 2(c) for both the normal and diseased valves.

In the methods described herein, the atrial surface of the fitted boundary mesh of each leaflet is used for finite element analysis. At each node of the mesh, localized leaflet thickness is quantified as chord length, i.e. the distance between the two boundary patches $b^+$ and $b^-$ associated with each point m on the medial manifold, as shown in FIG. 3.

Finite Element Analysis

To obtain high-quality meshes for complex shapes such as mitral leaflets, the atrial sides of the leaflet surfaces acquired from semi-automated image analysis were first imported into HyperMesh 10.0 (Altair Inc.) as triangular elements, where raw nodal points were added, suppressed, or replaced to refine the leaflets' topological details without changing geometrical shape. The mesh quality criteria included element Jacobian, element size, minimum and maximum angles, and skewness. The refined triangulated leaflet surfaces were modeled as thin shells (type S3R). The thickness measurements acquired from the rt-3DTEE data were interpolated and assigned to each node in the refined leaflet mesh using Matlab (the Mathworks, Natick, Mass.). Leaflet tissue was assumed to be orthotropic and linearly elastic, with a Poisson's ratio of 0.49, and Young's modulus determined from excised porcine tissue data (Table 1). The coaptation area between the anterior and posterior leaflet was defined as an interface pair with coefficient of friction $\mu=0.3$. Thirty-two chordae originating from each papillary muscle tip were inserted symmetrically into the anterior and posterior leaflets along the free edges of the leaflets (primary chordae), or more peripherally (secondary chordae). Papillary muscle tips were modeled as single points hinged in space associated with rotational freedom only. Chordae tendinae were represented by strings connecting the papillary muscle tips to the insertion points on the leaflets, and modeled by a tension-only truss element (type T3D2). Commercial FEA software (ABAQUS/Explicit 6.9, HKS Inc. Pawtucket, R.I.) was used to analyze the deformation and resulting stress distribution in the mitral valve models, as previously described by the inventors in the afore-mentioned article. Systolic loading was accomplished via application of an 80 mmHg pressure gradient across the mitral valve. Stress, strain and displacement were recorded as output variables.

TABLE 1

Mitral valve material properties used in FEA model

| Parameter | Anterior leaflet | Posterior leaflet | Primary chordae | Secondary chordae |
|---|---|---|---|---|
| Cross-sectional Area (mm$^2$) | — | — | 0.4 | 0.7 |
| $E_{circumferential}$ (Pa) | $6.20 \times 10^6$ | $2.35 \times 10^6$ | $4.20 \times 10^7$ | $2.20 \times 10^7$ |
| $E_{radial}$ (Pa) | $2.10 \times 10^6$ | $1.887 \times 10^6$ | — | — |
| Poisson's Ratio | 0.49 | 0.49 | 0.49 | 0.49 |
| Density (kg/m$^3$) | $1.04 \times 10^3$ | $1.04 \times 10^3$ | $1.04 \times 10^3$ | $1.04 \times 10^3$ |

Results

Figure 4:
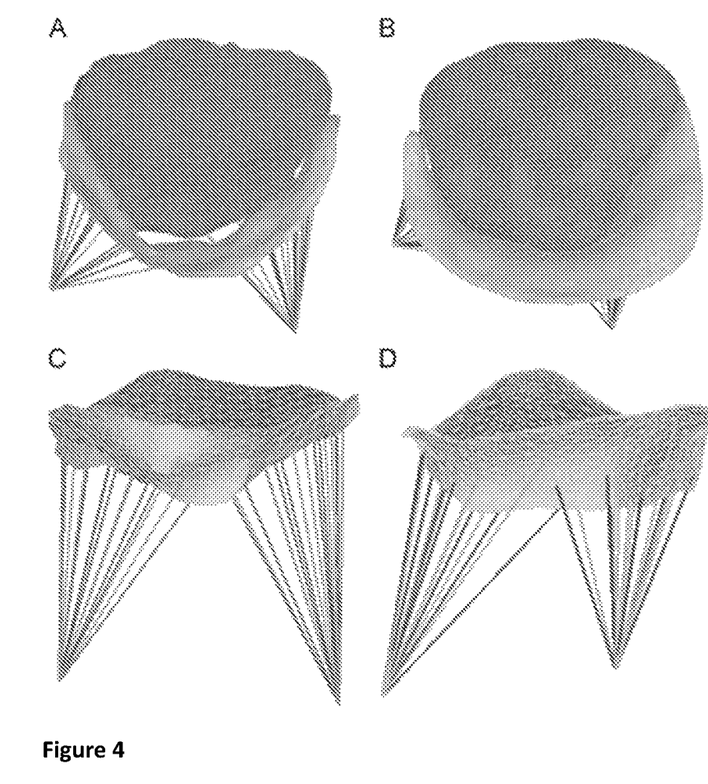
FIG. 4 illustrates finite element models of mid-systolic diseased (A, C) and normal (B, D) mitral valves reconstructed from rt-3DTEE, in transvalvular (A, B) and oblique (C, D) views.

The mean and maximal AL and PL thicknesses derived from 3DE are reported in Table 2, for both the normal and the diseased mitral valve. The regurgitant orifice of the diseased valve was clearly imaged and depicted in the 3D model, as demonstrated in FIG. 4. FIG. 4 illustrates finite element models of mid-systolic diseased (A, C) and normal (B, D) mitral valves reconstructed from rt-3DTEE, in transvalvular (A, B) and oblique (C, D) views. (Nodes and elements have been reduced for visualization purposes.)

Figure 5:
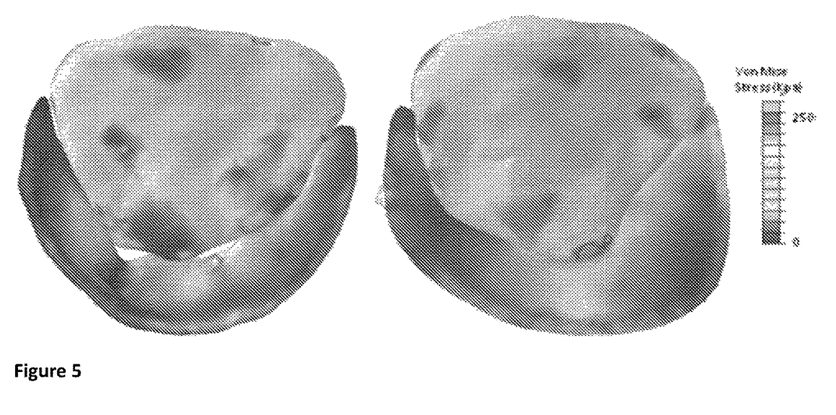
FIG. 5 illustrates von Mises stress contour maps of diseased (left) and normal (right) mitral valves.

FIG. 5 illustrates von Mises stress contour maps of diseased (left) and normal (right) mitral valves predicted by FEA. Note the persistent orifice between the anterior and posterior leaflets in the regurgitant valve despite some conformational change (deformation) with pressure loading. The regurgitant orifice of the diseased valve is evident in the loaded valve, though some conformational change (deformation) has occurred. The peak and mean stresses in the bellies of the AL and PL's of each valve were similar (Table 3). Note that for both mitral valves, the peak AL belly stress was larger than the peak PL belly stress, and the mean AL stress was significantly larger than the mean PL stress (P<0.001 in both the normal and the diseased valve).

TABLE 2

Mitral valve leaflet thicknesses

| | Mean (mm) | Maximum (mm) | Nodes in mesh |
|---|---|---|---|
| Anterior leaflet (normal) | 2.6 | 4.7 | 13735 |
| Posterior leaflet (normal) | 2.3 | 4.8 | 9148 |
| Anterior leaflet (diseased) | 2.4 | 5.1 | 9235 |
| Posterior leaflet (diseased) | 2.4 | 4.2 | 4125 |

TABLE 3 von Mises stress

| | Mean (kPa) | P-value | Peak (kPa) |
|---|---|---|---|
| Anterior leaflet belly (normal) | 97.1 ± 37.2 | | 215.5 |
| Posterior leaflet belly (normal) | 37.6 ± 14.4 | <.001 | 85.5 |
| Anterior leaflet belly (diseased) | 81.7 ± 19.2 | | 192.8 |
| Posterior leaflet belly (diseased) | 39.2 ± 16.3 | <.001 | 134.8 |

Discussion

A semi-automated and integrated methodology for imaging, segmenting, modeling, and deriving computationally-predicted pressure-derived mitral valve leaflet stresses is presented herein, and points the way towards intraoperative and periprocedural guidance from morphometric and stress modeling of the mitral valve.

The methods described herein provide an approach to valve morphometry that provides a comprehensive, automated assessment of 3D valve geometry—in both normal and diseased mitral valves—by ultrasound image analysis. This is accomplished using an efficient segmentation strategy that exploits the contrast in 3D transesophageal images and uses projections of 3D data to eliminate the need for the user to navigate a 3D image volume during initialization. Though not emphasized herein, the incorporation of deformable registration with cm-rep allows for a compact parametric representation of valve shape, from which a number of clinically significant features can be automatically derived. In addition, with the ability to establish points of correspondence on valves of different subjects and on the same valve at different time points, deformable modeling with cm-rep lays the foundation for statistical studies of time-dependent valve morphology.

A further advantage of the image analysis and segmentation algorithms described is that an objective measure of local mitral leaflet thickness is provided. While these measurements have not been validated in vivo, the inventors are in the process of doing so. Ex vivo human mitral valve leaflet thicknesses have been described, and the image-derived thicknesses are generally consistent with those pathologic measurements and with prior echocardiographic measures of leaflet thicknesses in normal human mitral valves. The present invention presents the first FEA simulation of the mitral valve incorporating high resolution in vivo measurements of leaflet thickness.

The ability to reliably estimate patient-specific mitral leaflet and chordal stresses in vivo has important clinical implications. Repair failure as manifest by the development of recurrent mitral regurgitation has recently been demonstrated to be far more common than originally believed. Recent studies have also shown that repair failures often result from stress related phenomenon such as chordal rupture, leaflet suture line disruptions and annuloplasty ring dehiscence. The ability to assess leaflet and chordal stresses in repaired valves will, with clinical experience, likely lead to improved surgical results by identifying patients with high stress valves in the early post-operative period. Such patients could either have re-repair or valve replacement before ever leaving the operating room, or could be subjected to closer post-operative clinical follow-up.

There are some evident limitations of the methods described herein. First, the stress maps derived have not been tested against in vivo experimental results. However, this deficit is characteristic of all prior work on the stress and strain behavior of the mitral valve apparatus: it is difficult or impossible to measure in vivo strains of heart valves except in discrete matrices of transducers or markers. Second, the FEA utilizes a less-than-comprehensive mitral valve model: whereas the leaflet surface profile and papillary muscle tips are accurately determined by rt-3DTEE, the chordae tendinae were not reliably imaged and so their incorporation in the model is, at best, heuristically motivated. This solution is admittedly suboptimal, but similar to that adopted in prior noninvasive mitral valve FEA studies (Votta, et al. 2008, "Mitral valve finite-element modeling from ultrasound data: a pilot study for a new approach to understand mitral function and clinical scenarios," Philosophical transactions Series A, Mathematical, physical, and engineering sciences, 366, pp. 3411-3434). Prot et. al. used ex vivo examination of porcine valves to determine the number and insertions of secondary chordae (Prot et al., "Finite element analysis of the mitral apparatus: annulus shape effect and chordal force distribution," Biomechanics and Modeling in Mechanobiology, Vol. 8, pp. 43-55), but this approach is clearly impossible in most human studies. In addition, the material properties model (linearly elastic) used is relatively simplified; however, the closed mitral valve has been shown to have a linear stress-strain relationship over the physiologic range of pressures. Finally, homogeneous and uniform material properties were used in implementing the methods described herein. It is reasonable to presume that leaflet material properties will be different in diseased and healthy mitral valves, and may vary regionally in a single valve. Nevertheless, the current research emphasizes the dependence of mechanical stress on geometric derangements in the diseased mitral valve.

Recently, the inventors have demonstrated that FEA modeling of the in vivo human mitral valve using high-resolution 3D imaging is reasonable and useful for stress prediction in mitral valve pathologies and repairs (Xu). The methods described herein extend and amplify those results, and promises near-real-time stress analysis in the human mitral valve using automated 3DE image analysis and modeling, and FEA. Therefore, a rational approach to in vivo mitral valve stress analysis incorporates realistic empiric material properties of leaflets and chordae, 3D imaging, semi-automated valve segmentation and modeling, and FEA.

Those skilled in the art will also appreciate that the invention may be applied to other applications and may be modified without departing from the scope of the invention. For example, the techniques described herein are not limited to measurement of mitral valve morphometry but also may be applied to other heart valves as well. Also, the methods of the invention may be applied to images obtained using other imaging methods besides echocardiography that permit quantification of the thickness of the heart valves. In addition, other segmentation methods, such as manual tracing or multi-atlas segmentation, may also be applied before the cm-rep model fitting. Another possibility is to fit the cm-rep model directly to the three-dimensional grayscale image. Accordingly, the scope of the invention is not intended to be limited to the exemplary embodiments described above, but only by the appended claims.

What is claimed:

1. A method of measuring or estimating stress distributions on heart valve leaflets in a subject, comprising:
   obtaining three-dimensional images of the heart valve leaflets;
   segmenting the heart valve leaflets in the three-dimensional images, in order to obtain three-dimensional binary images of the heart valve leaflets from which localized measurements of leaflet thickness can be computed;
   obtaining localized measurements of leaflet thickness by modeling a shape of each heart valve leaflet with three-dimensional medial axis representation, in order to generate an image-derived patient-specific model of the heart valve leaflets; and
   applying the image-derived patient-specific model of the heart valve leaflets to a finite element analysis (FEA) algorithm to estimate stresses on the heart valve leaflets.

2. The method of claim 1, wherein the obtaining step comprises imaging the heart valve leaflets using echocardiography to obtain three-dimensional ultrasound images.

3. The method of claim 1, wherein segmenting the heart valve leaflets is performed manually with active contour evolution, with multi-atlas segmentation, or with a deformable modeling method.

4. The method of claim 3, wherein the heart valve leaflets are segmented in the three-dimensional image data by user-initialized three-dimensional active contour evolution based on region competition.

5. The method of claim 4, wherein segmenting the heart valve leaflets further comprises user-initialized region of interest (ROI) extraction including construction of a two-dimensional maximum intensity projection image along an axial dimension of an image volume of the heart valve leaflet images and application of adaptive histogram equalization to the projection image to enhance an annular rim and leaflet coaptation zone of the heart valve.

6. The method of claim 5, wherein segmenting the heart valve leaflets further comprises a user outlining the heart valve and marking a leaflet coaptation curve in the enhanced projection image, selecting a threshold for region competition, and using resulting information to initialize said three-dimensional active contour evolution.

7. The method of claim 6, wherein segmenting the heart valve leaflets further comprises using a level set method to solve for a final three-dimensional segmentation.

8. The method of claim 1, further comprising obtaining a patient-specific cm-rep of the heart valve leaflets by fitting a deformable medial model to binary segmentations of the heart valve leaflets by Bayesian optimization.

9. The method of claim 1, wherein each heart valve leaflet is treated as a separate shape whose morphological skeleton comprises a single medial manifold.

10. The method of claim 9, wherein the medial manifold and surface boundaries of the cm-rep of each heart valve leaflet is discretely represented by a triangulated mesh and each node of the mesh quantifies a localized leaflet thickness measurement defined as a chord length or distance between two boundary points associated with that node on the mesh.

11. The method of claim 10, wherein during the Bayesian optimization the mesh of each heart valve leaflet is deformed such that a similarity between the mesh and its corresponding segmentation is maximized.

12. The method of claim 11, wherein a Laplace eigenfunction basis is defined on the mesh during fitting of the deformable medial model such that the mesh is deformed smoothly by modifying coefficients of a small number of basis functions rather than all vertices of the mesh.

13. The method of claim 12, wherein the fitting of the deformable medial model is performed in stages with increasing resolution.

14. The method of claim 1, wherein an atrial surface of the fitted cm-rep of each heart valve leaflet is applied to the FEA algorithm for finite element analysis using locally defined leaflet thickness at each point on the atrial surface as input.

15. The method of claim 1, wherein the segmenting step includes quantifying locally varying thicknesses of the heart valve leaflets in the three-dimensional image data.

16. The method of claim 15, wherein quantifying locally varying thicknesses of the heart valve leaflets in the three-dimensional image data comprises applying a deformable medial model that derives locally varying heart valve leaflet thickness measurements from a medial axis representation of the heart valve leaflets.

17. The method of claim 16, wherein the patient-specific model of the heart valve leaflets is applied to said FEA algorithm using image-derived thickness measurements of the heart valve leaflets as input material parameters.

18. The method of claim 1, wherein the heart valve is the mitral valve.

* * * * *

UNITED STATES PATENT AND TRADEMARK OFFICE
CERTIFICATE OF CORRECTION

PATENT NO. : 10,235,754 B2
APPLICATION NO. : 15/697169
DATED : March 19, 2019
INVENTOR(S) : Jackson et al.

It is certified that error appears in the above-identified patent and that said Letters Patent is hereby corrected as shown below:

On the Title Page

On Page 2, Column 2, Lines 17-21 References cited under OTHER PUBLICATIONS:
Replace "TVotta, et al., "Mitral Valve Finite-Element Modeling from Utrasound Data: A Pilot Study for a New Approach to Understand Mitral Function and Clinical Scenarios", Philosophical Transactions Series A, Mathematical, Physical, and Engineering Sciences, 366,July 2008, 3411-3434"

With:
--TVotta, et al., "Mitral Valve Finite-Element Modeling from Ultrasound Data: A Pilot Study for a New Approach to Understand Mitral Function and Clinical Scenarios", Philosophical Transactions Series A, Mathematical, Physical, and Engineering Sciences, 366, July 2008, 3411-3434--.

Signed and Sealed this
Twenty-seventh Day of August, 2019

Andrei Iancu
*Director of the United States Patent and Trademark Office*